United States Patent [19]
Kirst et al.

[11] Patent Number: 5,106,961
[45] Date of Patent: Apr. 21, 1992

[54] ERYTHROMYCIN RING-CONTRACTED DERIVATIVES

[75] Inventors: Herbert A. Kirst, Indianapolis; Julie A. Wind, Greenwood, both of Ind.

[73] Assignee: Eli Lilly and Company, Indianapolis, Ind.

[21] Appl. No.: 307,556

[22] Filed: Feb. 7, 1989

Related U.S. Application Data

[63] Continuation-in-part of Ser. No. 53,641, May 26, 1987, abandoned.

[51] Int. Cl.$^5$ .............................................. C07H 17/08
[52] U.S. Cl. ..................................... 536/7.2; 536/7.1; 536/18.1
[58] Field of Search ........................ 536/7.1, 7.2, 18.1

[56] References Cited

U.S. PATENT DOCUMENTS 4,677,097 6/1987 Omura et al. ........................ 514/29

OTHER PUBLICATIONS

Issac O. Kibwage et al., "Translactonization in Erythromycins," *J. Org. Chem.*, 52, 990–996 (1987).
Issac O. Kibwage, "Identification of Novel Erythromycin Derivatives in Mother Liquor Concentrates of *Streptomyces erythraeus*," *J. Antibiotics* 40(1), 1–6 (1987).
Arthur A. Nagel et al., "Macrolide Fundamental Chemistry: Sequential Conversion of the 14—Membered Ring Macrolide Antibiotic Oleandomycin to 12— and 10—Membered Ring Macrocyclic Lactone Systems," *J. Org. Chem.* 51, 5397–5400 (1986).
I. O. Kibwage et al., "Isolation of Erythromycins and Related Substances from Fermentation Residues of *Streptocmyces erythreus* by High-Performance Liquid Chromatography on Silica Gel," *J. Chromatogr.* 346, 309–319 (1985).
P. Kurath et al., "Acid Degradation of Erythromycin A and Erythromycin B," *Experientia* 27, 362 (1971).
S. Omura, Ed., *Macrolide Antibiotics*, Academic Press, N.Y. 1984, pp. 3–5, 9, 29–30, 85, 89–92, 120–121, 509, 529–531, 547.
K. Krowicki et al., "Chemical Modification of Erythromycins. II. 8-Hydroxy-Erythromycin A," *J. Antibiotics* 26, 575–581 (1973).
K. Krowicki et al., "Chemical Modifications of Erythromycins. IV. 8-Hydroxy-Erythromycin B," *J. antibiotics* 26, 587–592 (1973).
P. Kurath et al., "C(8) Epimeric 8-Hydroxy-Erythromycins-B," *Helv. Chim. Acta* 56, 1557–1565 (1973).
J. Tadanier et al., "C(8) Epimeric 8-14 Hydroxy-Erythromycins-A," *Helv. Chim. Acta* 56, 2711–2719 (1973).
H. Bojarska-Dahlig et al., "Some Modifications of the Aglycone Lactone Ring of Erythromycin A," *Rec. Trav. Chim. Pays-Bas* 92, 1305–1307 (1973).
Kibnage et al., "Translactonization in Erythromycins", J. Org. Chem. (1987), vol. 52 pp. 990–996.

*Primary Examiner*—Johnnie R. Brown
*Assistant Examiner*—Elli Peselev
*Attorney, Agent, or Firm*—Nancy J. Harrison; Leroy Whitaker

[57] ABSTRACT

Novel 12-membered lactone and 11-membered lactone derivatives of erythromycin, having antimicrobial activity against certain Gram-positive pathogens such as *Steptococcus pyogenes* and Gram-negative cocci such as *Haemophilus influenzae*, and useful as intermediates to other macrolide derivatives, are disclosed.

19 Claims, 2 Drawing Sheets

ERYTHROMYCIN RING-CONTRACTED DERIVATIVES

CROSS-REFERENCE TO RELATED APPLICATIONS

This application is a continuation in-part of copending application Ser. No. 07/053,641, filed May 26, 1987, now abandoned.

SUMMARY OF THE INVENTION

This invention relates to novel 12-membered lactone and 11-membered dilactone derivatives of erythromycin. These ring-contracted macrolides have antimicrobial activity against certain Gram-positive pathogens such as *Streptococcus pyogenes* and Gram-negative cocci such as *Haemophilus influenzae*. In addition, these compounds contribute to the understanding of structure-activity relationships in erythromycin-related compounds and should be useful as intermediates to other macroli derivatives.

DESCRIPTION OF THE DRAWINGS

In FIG. 1, erythromycin is abbreviated "EM", and in FIG. 2 m-chloroperbenzoic acid is abbreviated "MCPBA".

DETAILED DESCRIPTION OF THE INVENTION

This invention relates to novel macrolide antibiotics, which are 12-membered lactone and 11-membered dilactone derivatives of erythromycin, and to the salts and ester derivatives of these compounds.

New, improved antibiotics are continually in demand. In addition to antibiotics which are useful for treating human diseases, improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer body half life, and more advantageous rate or route of excretion and rate or pattern of metabolism) are some of the goals for improved antibiotics.

The macrolide antibiotic erythromycin has been the subject of much study, and a number of interesting derivatives such as erythromycylamine, 6-O-methylerythromycin and 8-fluoroerythromycin have been prepared. Making changes in the size of the macrolide ring itself, however, has not been extensively reported. Thus, it was quite surprising to discover methods for making the ring-contracted erythromycin derivatives of this invention.

This invention provides two new groups of ring-contracted macrolides. The first group of derivatives have the structure shown in the formula 1.

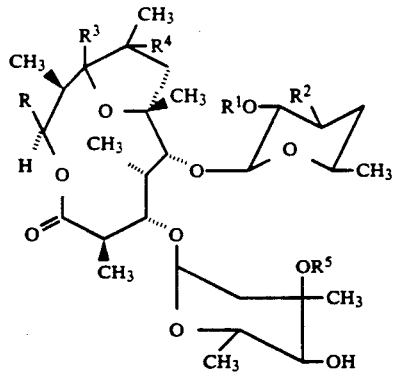

wherein

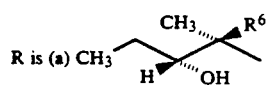

$R^1$ is hydrogen or $C_1$–$C_5$-alkanoyl;
$R^2$ is —$N(CH_3)_2$ or —$N(CH_3)_2 \rightarrow O$;
$R^3$ and $R^4$ are 1) either both hydroxyl or 2) taken together from a double bond;
$R^5$ is hydrogen or methyl; and
$R^6$ is hydrogen or hydroxyl; or a salt thereof.

The second group of ring-contracted derivatives of this invention have general formula 2

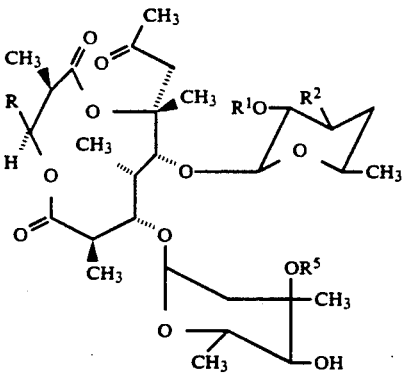

wherein R, $R^1$, $R^2$, $R^5$ and $R^6$ are as defined, or a salt thereof.

Figure 1:
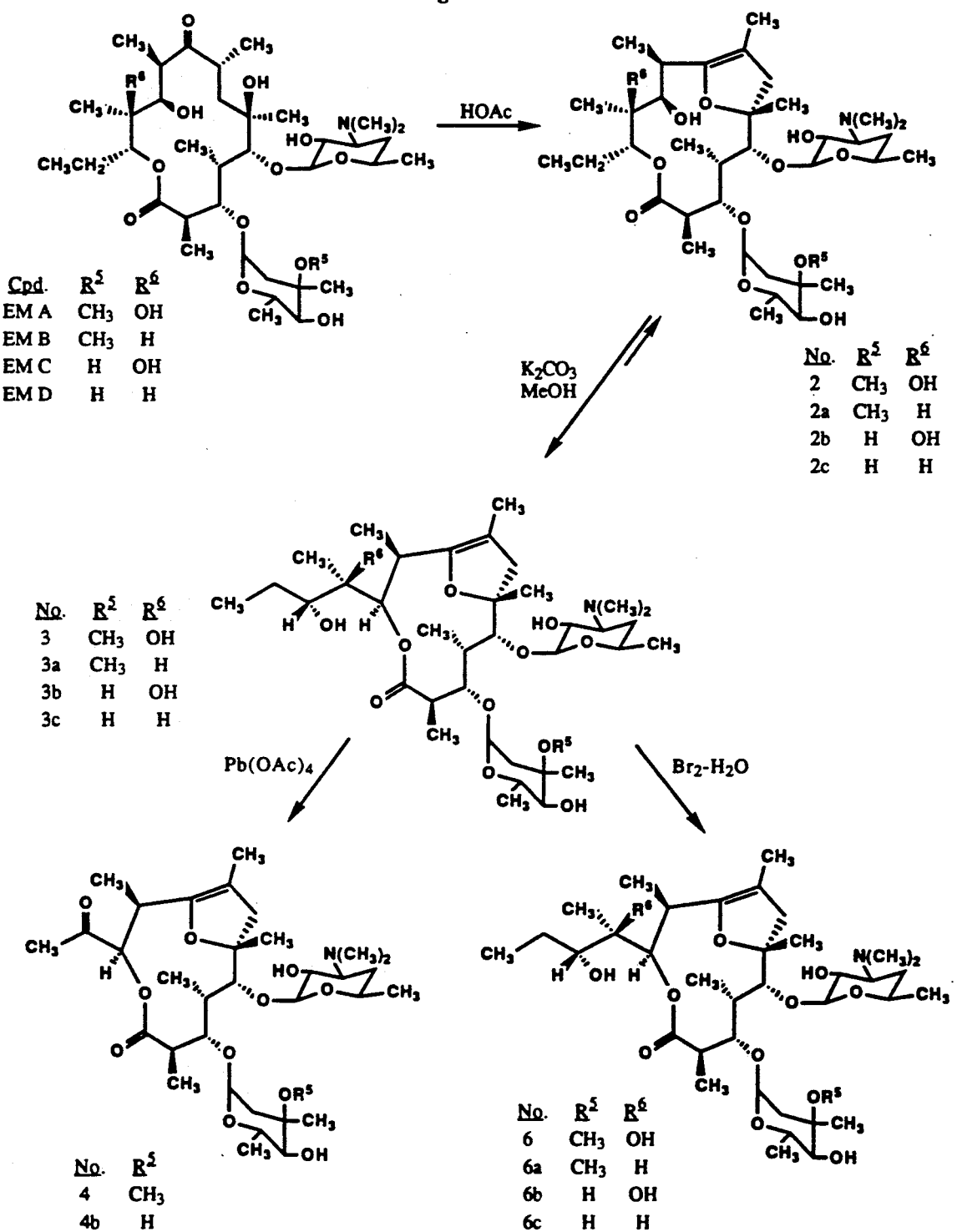
FIG. 1 shows the reaction sequences used to prepare Formula 1 compounds.

Four erythromycin factors are known. The structures of the commercial antibiotic erythromycin (also known as erythromycin A) and of erythromycins B, C and D are shown in FIG. 1.

The compounds of formulas 1 and 2 wherein $R^5$ is methyl and $R^6$ is hydroxyl are especially preferred compounds of this invention.

Acid-catalyzed conversion of erythromycin to its 8,9-anhydro-6,9-hemiketal derivative (compound 2) is well known. We have found that the lactone carbonyl group in this enol ether derivative (2) can migrate from the C-13 hydroxyl to the C-11 hydroxyl group under a wide variety of reaction conditions to yield a 12-membered ring enol ether derivative, i.e. the compound of formula 1 wherein R is an (a) group, $R^1$ is hydrogen, $R^2$ is —$N(CH_3)_2$, $R^3$ and $R^4$ together form a double bond, $R^5$ is methyl and $R^6$ is hydroxyl (compound 3). This translactonization process occurs under a variety of both acidic and basic conditions as well as thermally (in refluxing toluene). Furthermore, the acyl migration is reversible in many of these cases, so that an equilibrium between compounds 2 and 3 is established.

A preferred method for preparing compound 3 from compound 2 uses potassium carbonate in refluxing methanol. This method gives a mixture of compound 3 and compound 2 in a ratio of approximately 6:1 (HPLC analysis); however, isolation of compound 3 on a multigram scale is relatively easy, using well known procedures such as extraction and chromatography.

Unfortunately, trans-lactonization using potassium carbonate in refluxing methanol has been confined to the enol ether 2. Erythromycin itself as well as erythromycylamine, erythromycin-9-hydrazone, erythromycin anhydro-6,9;9,12-spiroketal and 9-dihydroerythromycin all failed to give any detectable conversion to ring-contracted products.

The transformation of compound 2 to compound 3 has been accomplished by conditions as diverse as 1) potassium carbonate in refluxing toluene or tetrahydrofuran (THF), 2) triethylamine in refluxing methanol, 3) 9-borabicyclo[3.3.1]nonane (9-BBN) in TH, 4) mercuric acetate in methanol and 5) iron pentacarbonyl in refluxing toluene, with trans-lactonization being the only apparent reaction.

The compounds of formulas 1 and 2 wherein R is acetyl are prepared by selectively cleaving the diol tail in those compounds of formulas 1 and 2 wherein R is an (a) group. Selective cleavage can be accomplished with suitable oxidizing agents such as lead tetra-acetate in inert solvents such as toluene.

The formula 1 and 2 compounds wherein $R^2$ is —N(CH$_3$)$_2$→O are prepared by oxidizing the formula 1 and 2 compounds wherein $R^2$ is —N(CH$_3$)$_2$. For example, compounds 3-3c yield the corresponding N-oxides 5-5c, respectively. Hydrogen peroxide or peracids such as m-chloroperbenzoic acid (MCPBA) are preferred oxidizing agents. The reverse transformation, i.e. —NMe$_2$→O to —NMe$_2$, can be achieved by reducing agents such as phosphorus(III) reagents (e.g. triphenylphosphine and tributylphosphine) or trialkylboranes (e.g. (sec-Bu)$_3$B).

The compounds of formula 1 wherein $R^3$ and $R^4$ are both hydroxyl are prepared by oxidizing the double bond in those formula 1 compounds wherein $R^3$ and $R^4$ together form a bond. Suitable oxidizing agents for this reaction are bromine, N-bromosuccinimide or N-chlorosuccinimide in solvents such as aqueous acetonitrile.

The compounds of formula 2 wherein R is an (a) group, $R^1$ is hydrogen and $R^2$ is —N(CH$_3$)$_2$→O are prepared by treating the ring-contracted enol ether compound (3) with m-chloroperbenzoic acid in dichloromethane at 0° C. This reaction gives a mixture of products from which the 11-membered-ring diolide N-oxide can be isolated as the principal component, albeit in low yield.

The compound of formula 2 wherein R is acetyl, $R^1$ is hydrogen and $R^2$ is —N(CH$_3$)$_2$ is prepared by treating compound 3 with sodium periodate in aqueous acetonitrile.

The derivatives of this invention wherein $R^2$ is —N(CH$_3$)$_2$ can form salts, particularly acid addition salts. These acid addition salts are also useful as antibiotics and are a part of this invention. In another aspect, such salts are useful as intermediates, for example, for separating and purifying the derivatives. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic, and like acids.

Pharmaceutically acceptable acid addition salts are an especially preferred group of salts of this invention. Pharmaceutically acceptable acid addition salts are those salts useful in the chemotherapy of a warm-blooded animal.

The compounds of formulas 1 and 2 wherein $R^1$ is $C_1$–$C_5$-alkanoyl are prepared by esterifying the appropriate 1 and 2 compounds wherein $R^1$ is hydrogen by treatment with acylating agents, using standard methods well exemplified in the art (see, for example, Baltz et al. in U.S. Pat. No. 4,321,361).

The new derivatives of this invention have antibacterial activity, but should be most valuable as intermediates to novel antibacterial agents.

The compounds of formulas 1 and 2 inhibit the growth of certain pathogenic bacteria, especially Gram-positive bacteria and Gram-negative cocci such as *Haemophilus influenzae*. Table I summarizes the minimal inhibitory concentrations (MIC's) at which these compounds inhibit certain organisms, as determined by standard agar-dilution assays.

TABLE I

| Antibacterial Activity of Ring-Contracted Derivatives[a] | | | | | |
|---|---|---|---|---|---|
| | Compound Number[b] | | | | |
| Organism | 3 | 4 | 6 | 8 | 3a |
| *Staphylococcus aureus* X1.1 | —[f] | — | 128 | — | 64 |
| *Staphylococcus aureus* V41[c] | — | — | — | — | — |
| *Staphylococcus epidermidis* 270 | — | — | — | — | 64 |
| *Staphylococcus epidermidis* 222 | — | — | 64 | — | 64 |
| *Streptococcus pyogenes* C203 | 32 | 64 | 16 | 128 | 64 |
| *Streptococcus pneumoniae* Park I | 16 | 32 | 8 | 32 | 64 |
| *Streptococcus faecalis* X66 | 64 | 16 | 16 | 64 | 64 |
| *Streptococcus faecalis* 2041 | — | 128 | 64 | — | 64 |
| *Haemophilus influenzae* C.L.[d] | 32 | 16 | 8 | 64 | 128 |
| *Haemophilus influenzae* 76[e] | 32 | 16 | 8 | 64 | 128 |

Figure 2:
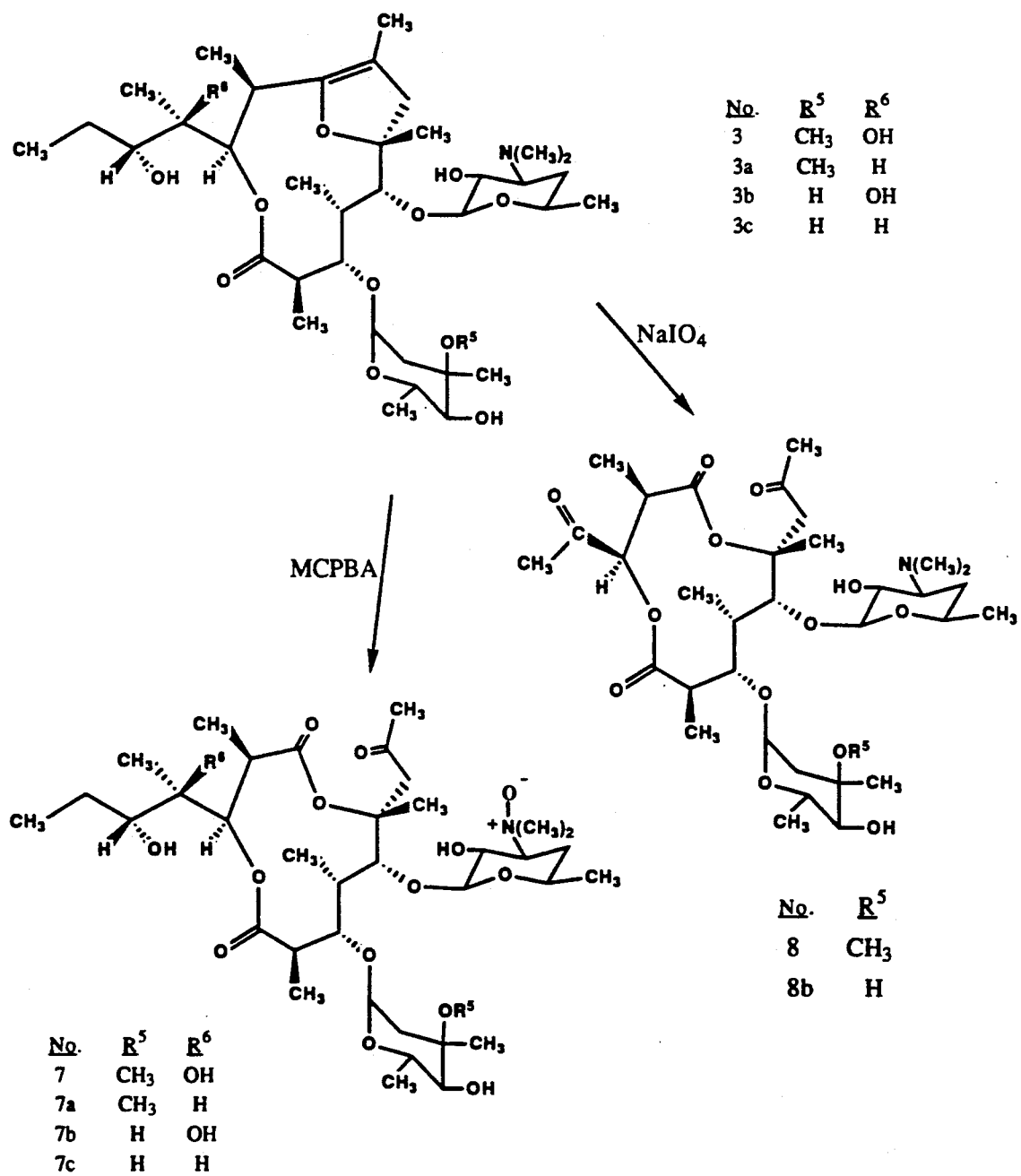
FIG. 2 shows the reaction sequences used to prepare Formula 2 compounds.

[a]MIC's in mcg/ml
[b]Compound numbers from FIGS. 1 and 2
[c]Penicillin-resistant strain
[d]Ampicillin-sensitive strain
[e]Ampicillin-resistant strain
[f]>128

The following examples are provided in order to illustrate this invention.

Product purification by chromatography was performed on silica gel, using either flash chromatography techniques (E. Merck grade 60 silica gel, 230–400 mesh) or a Waters Model 500 Prep LC system.

Compounds were purified to homogeneity according to thin layer chromatographic (TLC) and proton NMR analyses.

Preparation 1

8,9-Anhydro-erythromycin-6,9-hemiketal (Compound 2)

A solution of erythromycin (20.0 g, 27.3 mmol) in glacial acetic acid (100 mL) was stirred at room temperature for 1 hour. Sodium hydroxide (5N) was slowly added until precipitation was complete after the mixture had cooled back to ambient temperature. The mixture was extracted twice with dichloromethane. The combined organic layers were extracted with saturated sodium bicarbonate solution, dried (sodium sulfate), filtered and evaporated. The crude product (18.9 g) was purified by preparative HPLC (linear gradient of dichloromethane to 7% methanol +0.5% ammonium hydroxide in dichloromethane) to yield Compound 2 (13.2 g, 68%) as a white solid.

Preparation 2

Preparation of 8,9-Anhydro-erythromycin B-6,9-hemiketal (Compound 2a)

A solution of erythromycin B (1.0 g, 1.4 mmol) in glacial acetic acid (10 mL) was stirred at room temperature for 6 hours, and the solution was evaporated to dryness in vacuo. The residue was dissolved in $CHCl_3$ (100 mL) and extracted with saturated $NaHCO_3$ solution (3×100 mL). The crude product was purified by silica-gel chromatography, eluting with a linear gradient of $CH_2Cl_2$ to $CH_2Cl_2/MeOH/NH_4OH$ (92.5:7.5:0.5) to give compound 2a (301 mg, 31% yield) as a white solid foam.

IR($CHCl_3$):1720 cm$^{-1}$
MS(FD):m/z=699 (M$^+$)

EXAMPLE 1

Compound 3 from Trans-lactonization of Compound 2

Compound 2 (10.0 g, 14 mmol) in methanol (200 mL) was treated with potassium carbonate (1.9 g, 14 mmol), and the mixture was refluxed for 90 min. Solvent was evaporated under reduced pressure, and the residue was partitioned between dichloromethane and saturated sodium bicarbonate solution. The organic layer was evaporated to give 9.6 g of a white foam. This foam was purified by preparative HPLC (linear gradient of dichloromethane to 7.5% methanol +0.5% ammonium hydroxide in dichloromethane) to yield Compound 3 (5.4 g, 54%) as a white solid. FDMS $m/e$ 715 (M+H)$^+$.

EXAMPLE 2

Compound 4 from Lead Tetraacetate Cleavage of Compound 3

Compound 3 (2.0 g, 2.8 mmol) was dissolved in toluene (80 mL) and treated with lead tetra-acetate (1.9 g, 4.2 mmol). After being stirred at room temperature for 50 min., the heterogeneous mixture was extracted twice with saturated sodium bicarbonate solution, dried (sodium sulfate), filtered and evaporated. The crude product (1.8 g) was separated by flash chromatography, eluting with a gradient of dichloromethane to dichloromethane-methanol-ammonium hydroxide (96:4:0.5), to give compound 4 (780 mg, 43%) as a white foam. FDMS $m/e$ 655 (M+H)$^+$; IR 1720 cm$^{-1}$ (ketone carbonyl).

EXAMPLE 3

Compound 5 from N-Oxidation of Compound 3

Compound 3 (100 mg 0.14 mmol) was dissolved in acetonitrile (1 mL) and water (0.5 mL) and then treated with 30% hydrogen peroxide (0.014 mL) dropwise. The reaction was stirred at room temperature for 2 days, during which a white solid precipitated. The heterogeneous mixture was partitioned between dichloromethane and saturated sodium bicarbonate solution. The organic layer was dried (sodium sulfate) and evaporated to give 60 mg (59%) of Compound 5. $^1$H NMR was like that of Compound 3 except: δ 4.45(1'), 3.76(2'), 3.39(3'), 1.96/1.38(4'), 3.59(5'), 1.27(5'—CH$^3$), 3.20(NMe$_2$); FDMS $m/e$ 731 (M+H)$^+$.

EXAMPLE 4

Compound 6 from Oxidation of Compound 3

Compound 3 (100 mg, 0.14 mmol) was dissolved in acetonitrile (1 mL) and water (0.5 mL) and cooled to 0° C. for 15 min. A solution of bromine (23 mg, 0.14 mmol) in water (1 mL) was added dropwise. After being stirred for 20 min. at 0° C., the reaction mixture was partitioned between dichloromethane and saturated sodium bicarbonate solution. The organic layer was dried (sodium sulfate), filtered and evaporated to give 85 mg of Compound 6 (81%) as a white solid. FDMS $m/e$ 749 (M+H)$^+$.

EXAMPLE 5

Diolide 7 from MCPBA Cleavage of Compound 3

Compound 3 (1.0 g, 1.4 mmol) was dissolved in dichloromethane (10 mL) and cooled at 0° C. for 30 min. A solution of m-chloroperbenzoic acid (80%, 870 mg, 0.42 mmol) was added dropwise to the cooled solution. Since conversion was incomplete after 2 hr. at 0° C. (TLC), additional m-chloroperbenzoic acid (435 mg, 0.21 mmol) in dichloromethane (5 mL) was added. After an additional 2 hr., no change was apparent by TLC. The mixture was extracted with 10% sodium bisulfite solution and then with saturated sodium bicarbonate solution. The organic layer was dried (sodium sulfate) and evaporated to give 390 mg of crude product, from which 98 mg (9%) of Compound 7 was obtained by crystallization from dichloromethane. FDMS $m/e$ 764 (M+H)$^+$; IR 1723 cm$^{-1}$ (lactone carbonyl).

EXAMPLE 6

Diolide 8 from Sodium Periodate Cleavage of Compound 3

Compound 3 (100 mg, 0.14 mmol) was dissolved in methanol (1 mL) and water (0.5 mL). Sodium periodate (240 mg, 1.12 mmol) was dissolved in water (3 mL), with the aid of sonication, and methanol (2 mL) and was then added dropwise, yielding a white precipitate. After stirring the heterogeneous mixture for 11 days at room temperature, it was partitioned between ethyl acetate and saturated sodium bicarbonate solution. The crude product (60 mg) was purified by flash chromatography, eluting with a gradient of dichloromethane to dichloromethane - methanol (23:2), to yield Compound 8 (45 mg, 47%) as a colorless glass. FDMS $m/e$ 687 (M+H)$^+$; IR 1727 cm$^{-1}$ (lactone carbonyl).

EXAMPLE 7

Compound 3a from Translactonization of Compound 2a

Compound 2a (1.0 g, ].4 mmol) was reacted as described in Example 1 to give compound 3a (845 mg, 85%) as a white solid foam.

IR($CHCl_3$): 1701 cm$^{-1}$
MS(FD): m/z=699(M$^+$)

TABLE II

Proton NMR Chemical Shifts of Macrolide Derivatives[a,b]

| Position | 2 | 3 | 4 | 6 | 7 | 8 | 3a |
|---|---|---|---|---|---|---|---|
| 2 | 2.74 | 2.83 | 2.80 | 2.81 | 2.81 | 2.85 | 2.78 |
| 3 | 4.09 | 4.29 | 4.23 | 4.00 | 4.08 | 4.03 | 4.24 |
| 4 | 1.88 | 1.7 | 1.72 | 2.02 | 2.14 | 2.13 | 1.70 |
| 5 | 3.89 | 3.70 | 3.67 | 3.48 | 3.74 | 3.80 | 3.68 |
| 7 | 2.65/1.97 | 2.78/2.03 | 2.75/2.01 | 2.81/2.00 | 3.15/2.84 | 3.18/3.02 | 2.76/2.02 |
| 10 | 2.79 | 2.93 | 3.19 | 3.04 | 2.84 | 3.13 | 2.79 |
| 11 | 3.47 | 5.06 | 5.25 | 5.02 | 5.25 | 5.44 | 4.72 |
| 12 | — | — | — | — | — | — | 1.62 |
| 13 | 4.86 | 2.83 | — | 3.03 | 2.98 | — | 3.20 |
| 13-$CH_2$ | 1.88/1.47 | ~1.6/~1.3 | — | 1.72/1.24 | 1.89/1.31 | — | 1.58/1.31 |
| 13-$CH_3$ | 0.88 | 0.98 | — | 1.02 | 0.97 | — | 0.89 |
| 2-$CH_3$ | 1.15 | 1.27 | 1.30 | 1.23 | 1.28 | 1.35 | 1.23 |
| 4-$CH_3$ | 1.10 | 1.10 | 1.07 | 1.11 | 1.12 | 1.07 | 1.08 |
| 6-$CH_3$ | 1.35 | 1.42 | 1.39 | 1.52 | 1.76 | 1.77 | 1.42 |
| 8-$CH_3$ | 1.57 | 1.55 | 1.55 | 1.37 | 2.19 | 2.15 | 1.54 |
| 10-$CH_3$ | 1.06 | ~1.2 | 0.98 | 1.17 | 1.37 | 1.15 | 1.04 |
| 12-$CH_3$ | 1.06 | ~1.2 | 2.09 | 1.32 | 1.14 | 2.15 | 0.88 |
| 1' | 4.44 | 4.33 | 4.31 | 4.23 | 4.46 | 4.40 | 4.33 |
| 2' | 3.21 | 3.20 | 3.17 | 3.25 | 3.66 | 3.18 | 3.20 |
| 3' | 2.44 | 2.48 | 2.46 | 2.56 | 3.34 | 2.45 | 2.46 |
| 4' | 1.68/1.26 | ~1.6/~1.2 | 1.62/1.25 | 1.75/1.24 | 1.89/1.31 | 1.68/~1.20 | 1.66/1.23 |
| 5' | 3.52 | 3.48 | 3.44 | 3.46 | 3.56 | 3.48 | 3.47 |
| 5'$CH_3$ | 1.24 | 1.19 | 1.22 | 1.20 | 1.23 | 1.22 | 1.22 |
| $N(CH_3)_2$ | 2.29 | 2.29 | 2.26 | 2.32 | 3.16/3.14 | 2.29 | 2.27 |
| 1" | 5.09 | 4.89 | 4.90 | 4.77 | 4.90 | 4.93 | 4.87 |
| 2" | 2.41/1.60 | 2.38/~1.5 | 2.35/1.55 | 2.33/1.54 | 2.35/1.53 | 2.36/1.57 | 2.36/1.54 |
| 4" | 3.06 | 3.03 | 3.00 | 3.00 | 3.01 | 3.02 | 3.00 |
| 5" | 4.09 | 4.05 | 4.02 | 4.05 | 3.94 | 3.99 | 4.04 |
| 5"-$CH_3$ | 1.32 | 1.33 | 1.30 | 1.23 | 1.27 | 1.29 | 1.23 |
| 3"-$CH_3$ | 1.26 | 1.21 | 1.22 | 1.20 | 1.23 | 1.24 | 1.32 |
| 3-$OCH_3$ | 3.36 | 3.28 | 3.26 | 3.23 | 3.29 | 3.28 | 3.28 |
| OH | 3.09 | NA[c] | NA | NA | NA | NA | NA |
| 4"-OH | 2.19 | NA | NA | NA | NA | NA | NA |

[a] Obtained in deuteriochloroform solution using a Bruker WM-270 NMR spectrometer; chemical shifts are reported in parts per million from internal tetramethylsilane.
[b] Number of the carbon atoms in all compounds corresponds to their respective initial positions in 2.
[c] NA means not assigned

TABLE III

C-13 NMR Chemical Shifts of Macrolide Derivatives[a,b]

| Position | 2 | 3 | 4 | 6 | 7 | 8 | 3a |
|---|---|---|---|---|---|---|---|
| 1 | 178.30 | 175.94 | 173.19 | 172.15 | 175.78 | 173.13 | 176.30 |
| 2 | 44.82 | 46.82 | 46.33 | 46.41 | 47.53 | 46.89 | 46.82 |
| 3 | 76.59 | 80.53 | 80.59 | 81.58 | 78.62 | 79.73 | 80.55 |
| 4 | 43.28 | 38.77 | 38.71 | 40.58 | 38.45 | 38.71 | 38.98 |
| 5 | 80.26 | 81.60 | 81.82 | 86.07 | 81.53 | 82.15 | 81.79 |
| 6 | 85.63 | 86.06 | 86.15 | 85.09 | 86.82 | 86.53 | 85.95 |
| 7 | 42.69 | 43.40 | 43.54 | 50.06 | 44.42 | 45.45 | 43.49 |
| 8 | 101.47 | 101.34 | 102.58 | 81.93 | 205.98 | 204.09 | 101.53 |
| 9 | 151.78 | 149.60 | 147.87 | 109.28 | 172.60 | 171.22 | 149.80 |
| 10 | 30.47 | 31.67 | 32.48 | 38.29 | 43.09 | 42.21 | 31.29 |
| 11 | 70.89 | 77.49 | 80.50 | 80.46 | 74.41 | 77.55 | 78.42 |
| 12 | 75.41 | 76.61 | 206.09 | 77.16 | NA[c] | 206.12 | 38.27 |
| 13 | 78.28 | 76.70 | — | 78.28 | 76.82 | — | 70.91 |
| 13-$CH_2$ | 21.07 | 22.50 | — | 22.79 | 22.86 | — | 26.66 |
| 13-$CH_3$ | 10.58 | 11.82 | — | 11.60 | 11.63 | — | 11.16 |
| 2-$CH_3$ | 13.50 | 15.14 | 14.78 | 14.70 | 14.33 | 14.57 | 15.34 |
| 4-$CH_3$ | 8.72 | 9.29 | 9.42 | 10.81 | 9.37 | 9.84 | 9.35 |
| 6-$CH_3$ | 26.23 | 26.69 | 26.92 | 32.11 | 23.72 | 24.95 | 26.93 |
| 8-$CH_3$ | 11.83 | 10.93 | 10.95 | 23.96 | 32.80 | 32.10 | 11.02 |
| 10-$CH_3$ | 14.81 | 11.20 | 10.60 | 15.11 | 11.51 | 11.19 | 8.99 |
| 12-$CH_3$ | 16.17 | 15.56 | 27.42 | 18.03 | 17.98 | 26.98 | 7.96 |
| 1' | 102.99 | 103.99 | 103.97 | 105.03 | 102.91 | 103.47 | 104.12 |
| 2' | 70.48 | 71.06 | 71.06 | 70.30 | 72.24 | 70.82 | 71.08 |
| 3' | 65.88 | 65.37 | 65.44 | 65.39 | 76.15 | 65.47 | 65.36 |
| 4' | 28.83 | 28.83 | 28.95 | 28.90 | 34.77 | 28.92 | 28.86 |
| 5' | 68.81 | 68.97 | 69.00 | 69.51 | 67.41 | 69.15 | 69.01 |
| 5'-$CH_3$ | 21.30 | 21.18 | 21.25 | 20.94 | 20.98 | 21.25 | 21.26 |
| $N(CH_3)_2$ | 40.33 | 40.25 | 40.30 | 40.36 | 59.06/52.09 | 40.33 | 40.30 |
| 1" | 94.77 | 97.53 | 97.47 | 98.33 | 96.56 | 96.82 | 97.39 |
| 2" | 34.73 | 35.25 | 35.33 | 35.41 | 34.86 | 35.15 | 35.32 |
| 3" | 73.05 | 72.42 | 72.47 | 72.51 | 72.53 | 72.65 | 72.47 |
| 4" | 78.21 | 78.13 | 78.18 | 78.06 | 77.91 | 77.91 | 78.18 |
| 5" | 65.60 | 65.37 | 65.44 | 65.45 | 65.50 | 65.71 | 65.36 |
| 5"-$CH_3$ | 18.25 | 18.33 | 18.42 | 17.34 | 18.28 | 18.16 | 21.51 |
| 3"-$CH_3$ | 21.56 | 21.44 | 21.51 | 21.40 | 21.57 | 21.57 | 18.43 |

TABLE III-continued

| C-13 NMR Chemical Shifts of Macrolide Derivatives[a,b] | | | | | | | |
|---|---|---|---|---|---|---|---|
| Position | 2 | 3 | 4 | 6 | 7 | 8 | 3a |
| 3″-OCH₃ | 49.50 | 49.30 | 49.36 | 49.08 | 49.48 | 49.36 | 49.38 |

[a]Obtained in deuteriochloroform solution using a Bruker WM-270 NMR spectrometer; chemical shifts are reported in parts per million using internal chloroform (77.0 ppm).
[b]Number of the carbon atoms in all compounds corresponds to their respective initial positions in 2.
[c]NA means not assigned.

TABLE IV

| TLC and HPLC Data for Macrolide Derivatives[a,b] | | |
|---|---|---|
| Compound Number[c] | TLC $R_f$ | HPLC $t_r$ (min) |
| 2 | 0.60 | 10.78 |
| 3 | 0.50 | 7.00 |
| 4 | 0.62 | 7.72 |
| 5 | 0.29 | 5.95 |
| 6 | 0.37 | 3.93 |
| 7 | 0.21 | 2.86 |
| 8 | 0.57 | 3.86 |

[a]TLC was performed using E Merck plates of silica gel 60 with a fluorescent indicator (F-254), dichloromethane-methanol-concentrated ammonium hydroxide (90:10:2) as the developing solvent and anisaldehyde-sulfuric acid spray reagent for detection.
[b]Analytical HPLC was performed on a Waters microbondapak C18 column with acetonitrile-methanol-1% ammonium acetate (30:30:40) as the mobile phase and a refractive index detector.
[c]Compound numbers from FIGS. 1–2.

We claim:

1. A compound of the formula

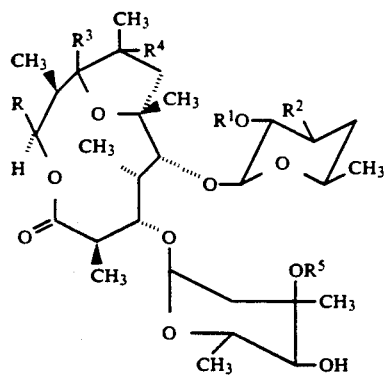

wherein
R is a)

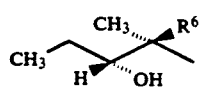

or b) acetyl;
$R^1$ is hydrogen or $C_1-C_5$-alkanoyl;
$R^2$ is —N(CH₃)₂ or —N(CH₃)₂→O;
$R^3$ and $R^4$ are hydroxyl;
$R^5$ is hydrogen or methyl; and
$R^6$ is hydrogen or hydroxyl; or a pharmaceutically acceptable salt thereof.

2. A compound of claim 1 wherein R is

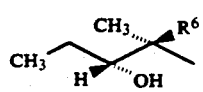

and $R^6$ is hydrogen or hydroxy.

3. A compound of claim 1 wherein $R^2$ is —N(CH₃)₂.
4. A compound of claim 1 wherein R is acetyl.
5. A compound of claim 1 wherein $R^2$ is —N(CH₃)₂→O.
6. A compound of claim 1 wherein $R^5$ is methyl and $R^6$ is hydroxyl.
7. A compound of claim 1 wherein $R^5$ is methyl and $R^6$ is hydroxyl.
8. A compound of claim 1 wherein $R^5$ is methyl and $R^6$ is hydrogen.
9. A compound of claim 1 wherein R is

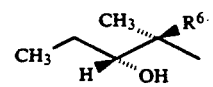

and $R^6$ is hydrogen or hydroxy.
10. A compound of claim 1 wherein $R^2$ is —N(CH₃)₂.
11. A compound of claim 1 wherein R is acetyl.
12. A compound of claim 1 wherein $R^2$ is —N(CH₃)₂→O.
13. A compound of claim 1 wherein $R^5$ is methyl and $R^6$ is hydroxyl.
14. A compound of the formula

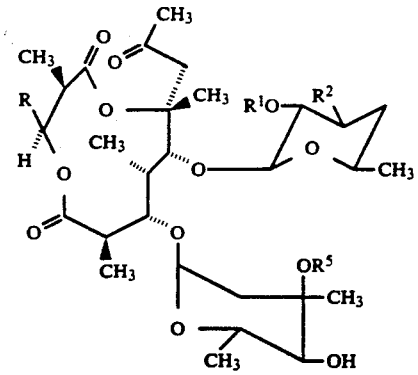

wherein
R is a)

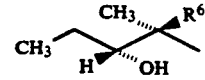

or b) acetyl:
$R^1$ is hydrogen or $C_1-C_5$-alkanoyl;
$R^2$ is —N(CH₃)₂ or —N(CH₃)₂→O;
$R^5$ is hydrogen or methyl; and
$R^6$ is hydrogen or hydroxyl; or a pharmaceutically acceptable salt thereof.

15. A compound of claim 14 wherein R is

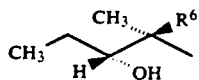
and $R^6$ is hydrogen or hydroxy.
16. A compound of claim 14 wherein $R^5$ is methyl and $R^6$ is hydrogen.
17. A compound of claim 14 wherein $R^5$ is methyl and $R^6$ is hydroxyl.
18. A compound of claim 14 wherein $R^2$ is —$N(CH_3)_2$.
19. A compound of claim 14 wherein R is acetyl.
* * * * *